United States Patent
Urbanowicz et al.

(10) Patent No.: US 11,980,560 B2
(45) Date of Patent: May 14, 2024

(54) ANKLE FOOT ORTHOTIC ASSEMBLY

(71) Applicants: Michael Urbanowicz, New Vienna, OH (US); Brittany Urbanowicz, New Vienna, OH (US)

(72) Inventors: Michael Urbanowicz, New Vienna, OH (US); Brittany Urbanowicz, New Vienna, OH (US)

( * ) Notice: Subject to any disclaimer, the term of this patent is extended or adjusted under 35 U.S.C. 154(b) by 116 days.

(21) Appl. No.: 17/154,102

(22) Filed: Jan. 21, 2021

(65) Prior Publication Data
US 2022/0226138 A1  Jul. 21, 2022

(51) Int. Cl.
*A61F 5/01* (2006.01)

(52) U.S. Cl.
CPC ................ *A61F 5/0113* (2013.01)

(58) Field of Classification Search
CPC ........ A61F 5/0102; A61F 5/14; A61F 5/0113; A61F 5/0111; A61F 5/0195; A61F 5/0585; A61F 5/0116; A61F 5/0127; A61F 5/30; A43B 7/00; A43B 7/14; A43B 11/00; A43B 7/1463; A43B 13/40; A43B 7/28; A43B 7/20; A43B 5/0405; A43B 3/02
See application file for complete search history.

(56) References Cited

U.S. PATENT DOCUMENTS

| | | | | |
|---|---|---|---|---|
| 2,832,336 A | * | 4/1958 | Clade | A43B 7/02 128/DIG. 20 |
| 3,087,260 A | * | 4/1963 | Hudon | A43B 3/20 36/7.2 |
| 4,550,721 A | * | 11/1985 | Michel | A43B 7/00 602/27 |
| 5,109,613 A | | 5/1992 | Van Dyke | |
| 5,143,058 A | * | 9/1992 | Luber | A61F 5/0585 602/28 |
| 5,430,960 A | | 7/1995 | Richardson | |

(Continued)

FOREIGN PATENT DOCUMENTS

| | | | | |
|---|---|---|---|---|
| KR | 20200135690 | * | 5/2019 | ............. A43B 3/244 |
| KR | 20200135690 A | * | 5/2019 | ............. A43B 3/244 |
| WO | WO9511604 | | 5/1995 | |

OTHER PUBLICATIONS

김우헌김상길 (Kim), "Detachable zip shoes for indoor and outdoor use", May 25, 2019, pp. 1-7 (Year: 2019).*

(Continued)

*Primary Examiner* — Alireza Nia
*Assistant Examiner* — Eric Richard McQuiggan
(74) *Attorney, Agent, or Firm* — Fitch, Even, Tabin & Flannery, LLP

(57) ABSTRACT

An ankle foot orthotic assembly for concealing an ankle foot orthotic worn by a user includes a boot that can be worn on a user's foot having the boot extending upwardly on the user's lower leg. The boot has a flap is integrated therein and the flap is positionable in an open position to enhance the user's ability to position their foot and lower leg into the boot. An ankle foot orthotic is integrated into the boot to engage the user's lower leg and the user's foot thereby facilitating the ankle foot orthotic to aid with foot drop syndrome in the user. Moreover, the ankle foot orthotic is positioned inside the boot thereby facilitating the ankle foot to be concealed from observers thereby enhancing the user's self-confidence.

8 Claims, 4 Drawing Sheets

(56) References Cited

U.S. PATENT DOCUMENTS

| | | | |
|---|---|---|---|
| 5,449,005 A | 9/1995 | Echols | |
| 5,678,330 A | 10/1997 | Van Dyke | |
| 5,833,639 A * | 11/1998 | Nunes | A61F 5/34 |
| | | | 128/882 |
| 5,865,778 A | 2/1999 | Jphnson | |
| 5,913,841 A | 6/1999 | Lamont | |
| 6,021,780 A * | 2/2000 | Darby | A61F 5/0111 |
| | | | 128/882 |
| 6,361,514 B1 * | 3/2002 | Brown | A61F 5/0111 |
| | | | 128/882 |
| 6,792,700 B2 | 9/2004 | Gallegos | |
| 6,860,864 B2 * | 3/2005 | Meyer | A61F 5/0111 |
| | | | 128/882 |
| 7,624,519 B1 * | 12/2009 | Thorne | A61F 5/0195 |
| | | | 36/110 |
| 10,178,893 B1 * | 1/2019 | Baker | A43B 23/0245 |
| 2014/0157624 A1 * | 6/2014 | Girard | A43B 3/06 |
| | | | 36/50.1 |
| 2014/0338228 A1 | 11/2014 | Rolle | |
| 2016/0051400 A1 * | 2/2016 | Ruetenik | A61F 7/103 |
| | | | 601/15 |
| 2019/0246737 A1 * | 8/2019 | Glidden-VerWeire | |
| | | | A43B 5/10 |

OTHER PUBLICATIONS

김우헌 (Kim), "detachable zip shoes for indoor and outdoor use" May 25, 2019, All pages (Year: 2019).*

* cited by examiner

ANKLE FOOT ORTHOTIC ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to orthotic devices and more particularly pertains to a new orthotic device for concealing an ankle foot orthotic worn by a user. The orthotic device is integrated into a boot such that the orthotic device is concealed from an observer. Additionally, the orthotic device has an open front side to facilitate easy the orthotic device to be easily worn.

(2) Description of Related Art Including Information Disclosed Under 37 CFR 1.97 and 1.98

The prior art relates to orthotic devices including a variety of boots that have an ankle foot orthotic integrated therein for treating foot drop syndrome. The prior art also discloses a variety of athletic shoes that has various means of rigid ankle supports integrated therein for enhanced ankle support of a user. The prior art additionally discloses a boot shaped cover for an ankle foot orthotic. In no instance does the prior art disclose a boot, having a flap to open the boot, in combination with an ankle foot orthotic being integrated into the boot.

BRIEF SUMMARY OF THE INVENTION

An embodiment of the disclosure meets the needs presented above by generally comprising a boot that can be worn on a user's foot having the boot extending upwardly on the user's lower leg. The boot has a flap is integrated therein and the flap is positionable in an open position to enhance the user's ability to position their foot and lower leg into the boot. An ankle foot orthotic is integrated into the boot to engage the user's lower leg and the user's foot thereby facilitating the ankle foot orthotic to aid with foot drop syndrome in the user. Moreover, the ankle foot orthotic is positioned inside the boot thereby facilitating the ankle foot to be concealed from observers thereby enhancing the user's self confidence.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
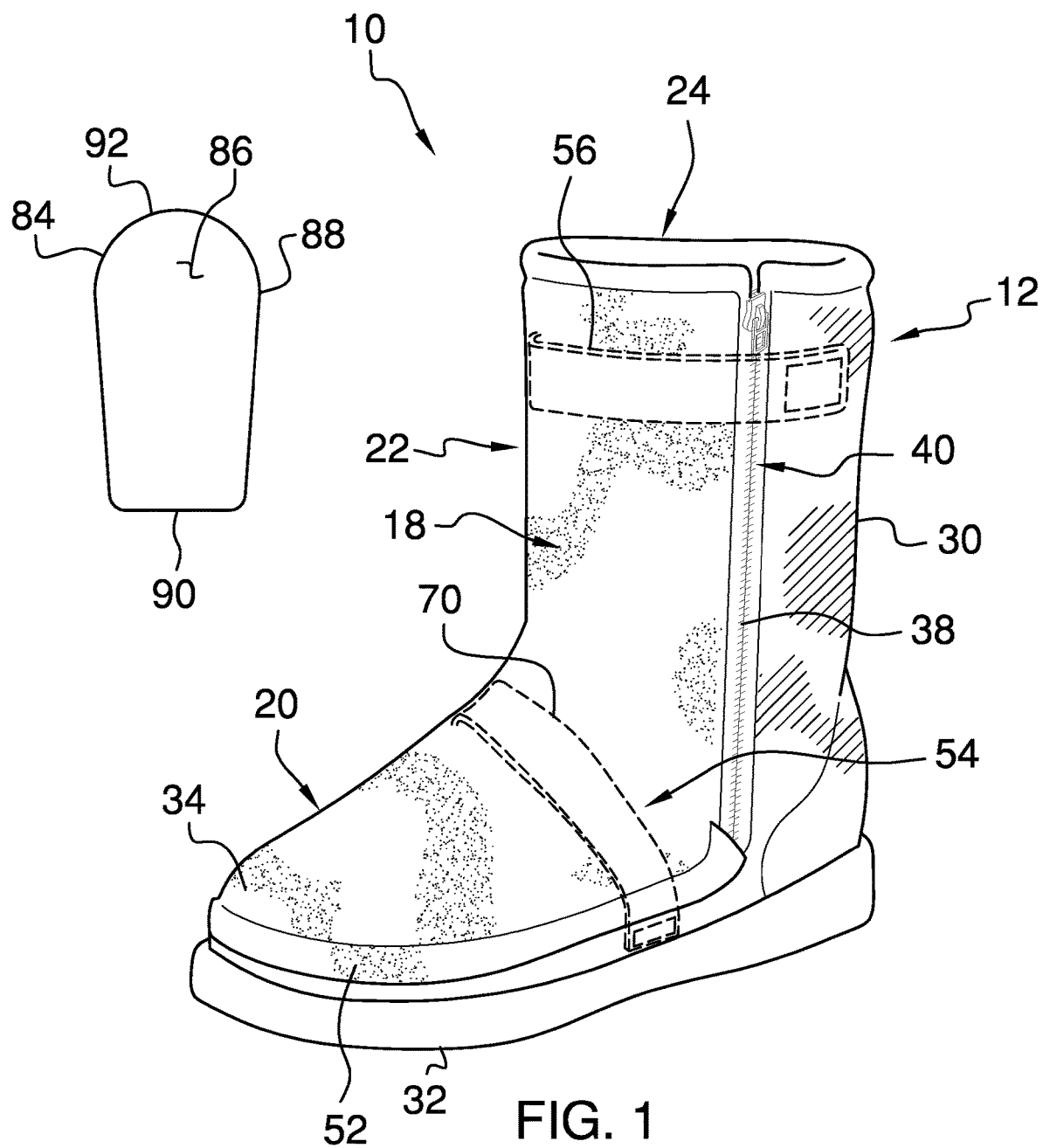
FIG. 1 is a perspective phantom view of an ankle foot orthotic assembly according to an embodiment of the disclosure.
Figure 2:
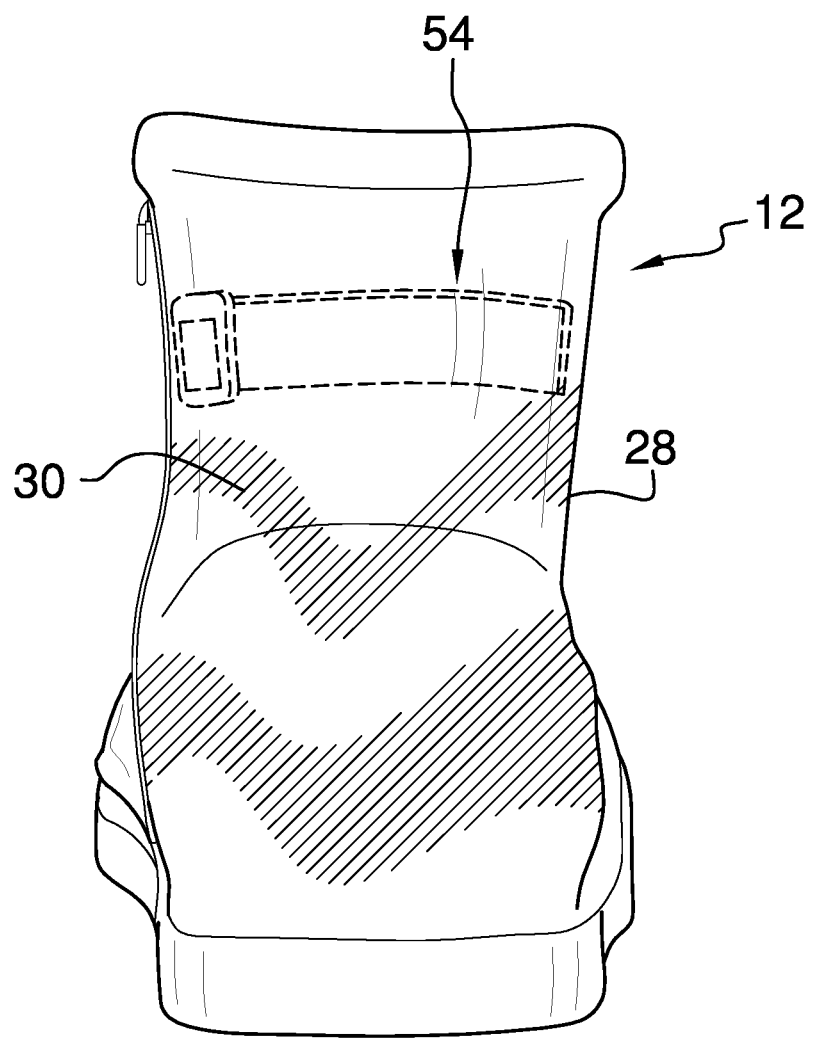
FIG. 2 is a back phantom view of an embodiment of the disclosure.
Figure 3:
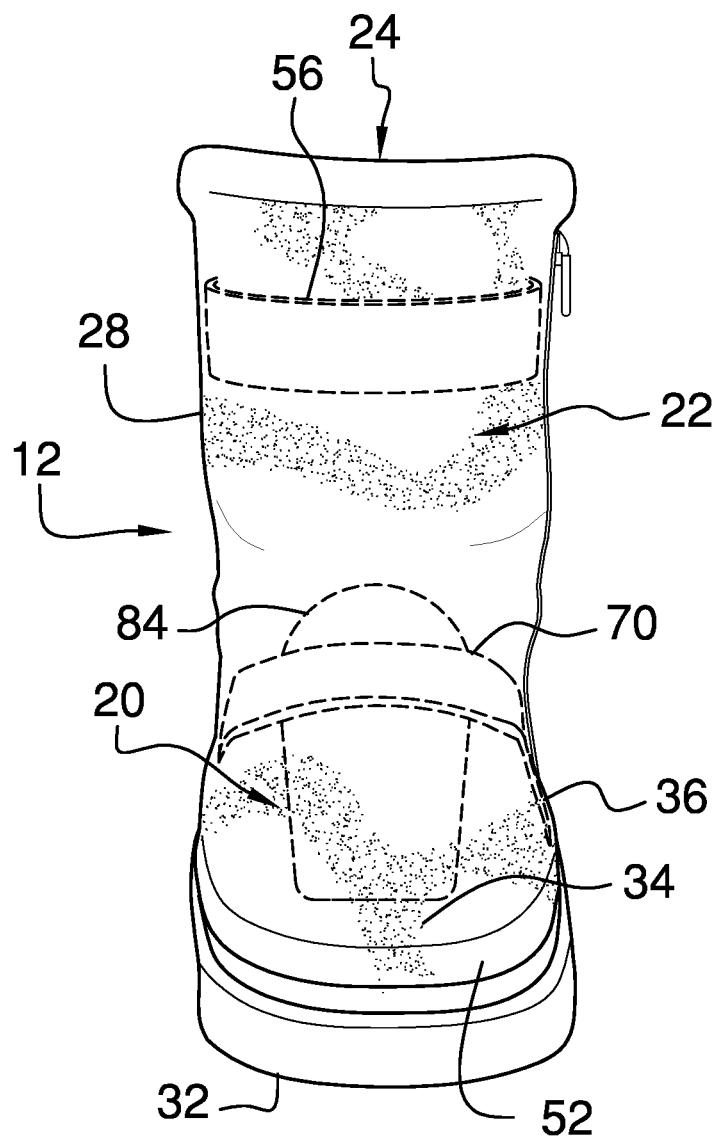
FIG. 3 is a front phantom view of an embodiment of the disclosure.
Figure 4:
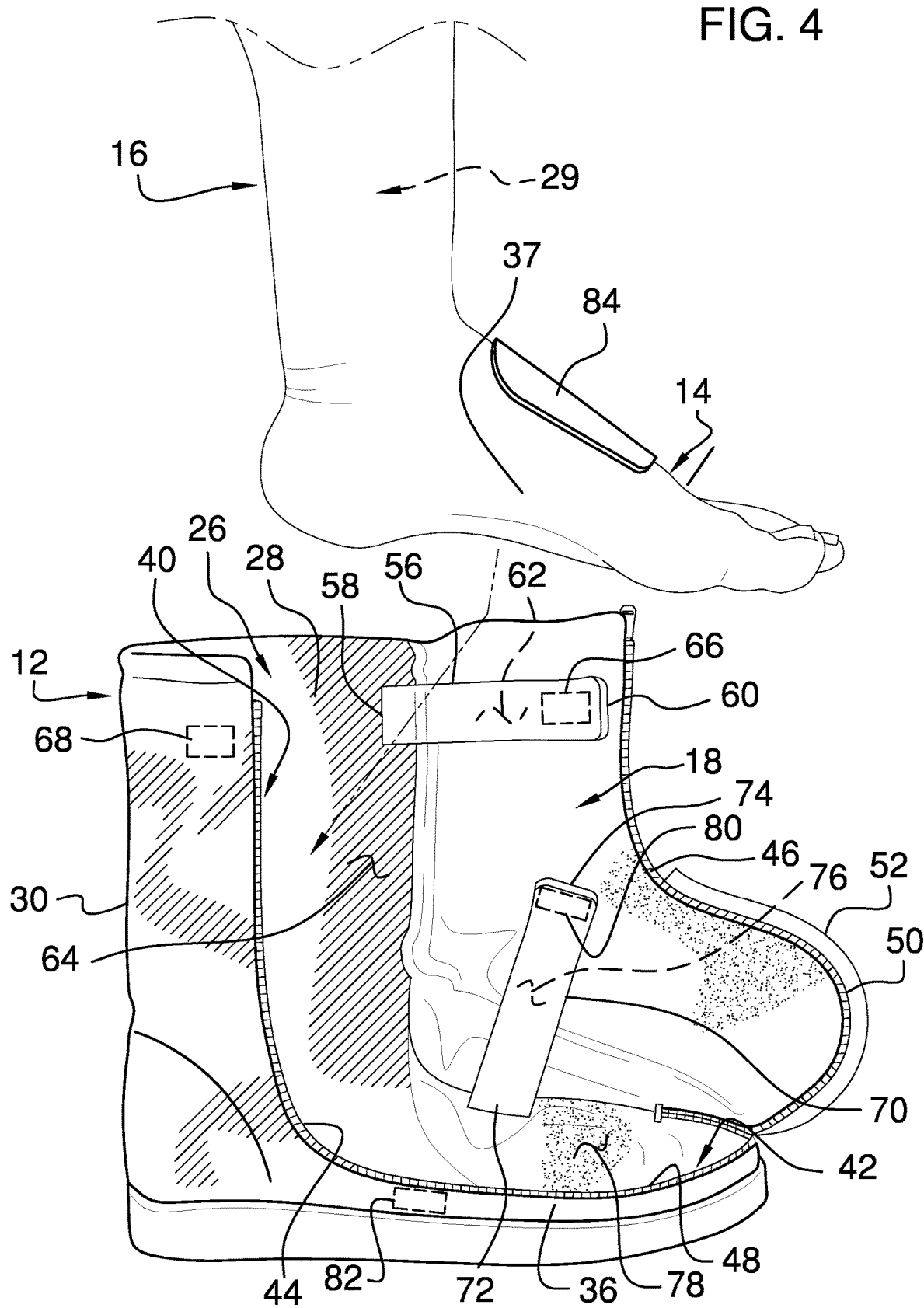
FIG. 4 is a perspective in-use view of an embodiment of the disclosure.

With reference now to the drawings, and in particular to FIGS. 1 through 4 thereof, a new orthotic device embodying the principles and concepts of an embodiment of the disclosure and generally designated by the reference numeral 10 will be described.

As best illustrated in FIGS. 1 through 4, the ankle foot orthotic assembly 10 generally comprises a boot 12 that can be worn on a user's foot 14 having the boot 12 extending upwardly on the user's lower leg 16. The user may be an individual with a physical disability that involves foot drop syndrome, such as a person that has suffered a stroke, a person that suffers from cerebral palsy or any other type of disability that involves foot drop syndrome. The boot 12 has a flap 18 integrated therein and the flap 18 is positionable in an open position thereby exposing an interior of the boot 12. In this way the flap 18 enhances the user's ability to position their foot 14 and lower leg 16 into the boot 12. Conversely, the flap 18 is positionable in a closed position retain the boot 12 on the user's foot 14 and lower leg 16.

The boot 12 has a foot portion 20 that surrounds the user's foot 14 and the boot 12 has a leg portion 22 extending upwardly from the foot portion 20 to surround the user's lower leg 16. The leg portion 22 has a top end 24 that is open to define an opening 26 into the leg portion 22 to facilitate the user's lower leg 16 to extend therethrough. The leg portion 22 has an outward side 28 that is positioned on a lateral aspect 29 of the user's lower leg 16 when the boot 12 is worn. Additionally, the leg portion 22 has a back quarter 30 and the back quarter 30 is comprised of a rigid material to assist with supporting the user's lower leg 16 and the user's foot 14 when the boot 12 is worn. The boot 12 may be comprised of leather or any other type of material that meets the user's preference for the overall style and appearance of the boot 12.

The foot portion 20 has a sole 32 and a toe 34, and the foot portion 20 has an inward side 36 that is positioned on a medial side 37 of the user's foot 14 when the boot 12 is worn. The boot 12 has a cut 38 extending therethrough, and the cut 38 has a first portion 40 extending downwardly from the top end 24 of the leg portion 22 along the outward side 28 of the leg portion 22. Additionally, the cut 38 has a second portion 42 extending along the foot portion 20 of the boot 12. The second portion 42 is spaced from the sole 32 and the second portion 42 is oriented to extend along a line that is oriented perpendicular to the first portion 40. Moreover, the second portion 42 extends around the toe 34 to terminate on the inward side 36 of the foot portion 20. In this way the first portion 40 and the second portion 42 of the cut 38 defines the flap 18, and the cut 38 has a first edge 44 and a second edge 46.

A first fastener 48 is coupled to the boot 12 and the first fastener 48 is coextensive with the first edge 44 of the cut 38. A second fastener 50 is coupled to the flap 18 and the second fastener 50 is mateable to the first fastener 48 for retaining the flap 18 in the closed position. The second fastener 50 is un-mateable from the first fastener 48 to facilitate the flap 18 to be positioned in the open position, and the second fastener 50 is coextensive with the second edge 46 of the cut 38. Each of the first fastener 48 and the second fastener 50 may comprise complementary halves of a zipper or other type of mechanically releasable fastening device.

A cover 52 is provided and the cover 52 is coupled to the boot 12. The cover 52 covers a substantial amount of the first fastener 48 and the second fastener 50 when the flap 18 is in the closed position. In this way the cover 52 inhibits an observer from seeing the first fastener 48 and the second fastener 50 thereby enhancing the user's self-confidence when the user is wearing the boot 12. The cover 52 is positioned on the foot portion 20 of the boot 12 and the cover 52 is coextensive with the second portion 42 of the cut 38. Moreover, the cover 52 extends downwardly over the second portion 42 of the cut 38 when the flap 18 is in the closed position for concealing the first fastener 48 and the second fastener 50 along the foot portion 20 of the boot 12. The boot 12 may be manufactured to custom specifications as required by orthotic specialists to facilitate a custom fit for any user.

An ankle foot orthotic 54 is integrated into the boot 12 and the ankle foot orthotic 54 engages the user's lower leg 16 and the user's foot 14 when the user wears the boot 12. In this way the ankle foot orthotic 54 can aid with foot drop syndrome in the user. The ankle foot orthotic 54 is positioned inside the boot 12 such that the ankle foot orthotic 54 is concealed from observers thereby enhancing user's self-confidence.

The ankle foot orthotic 54 comprises a first strap 56 that has a first end 58, a second end 60 and a first surface 62 extending therebetween, and the first strap 56 is elongated between the first end 58 and the second end 60. The first end 58 is coupled to an inside surface 64 of the back quarter 30 of the leg portion 22 of the boot 12 at a point that is located on an opposite side of the leg portion 22 with respect to the cut 38. Moreover, the first strap 56 is oriented to extend along a horizontal axis thereby facilitating the first strap 56 to be wrapped around the user's lower leg 16 when the user wears the boot 12. The first strap 56 is spaced from the top end 24 of the leg portion 22.

The ankle foot orthotic 54 includes a first mating member 66 that is coupled to the first surface 62 of the first strap 56. The first mating member 66 is positioned adjacent to the second end 60 of the first strap 56. Additionally, the ankle foot orthotic 54 includes a second mating member 68 that is coupled to the inside surface 64 of the back quarter 30 of the leg portion 22 of the boot 12 at a point is located adjacent to the first edge 44 of the cut 38. The second mating member 68 is positioned adjacent to the top end 24 of the leg portion 22 and the first mating member 66 is releasably mateable to the second mating member 68, Each of the first mating member 66 and the second mating member 68 may comprise a hook and loop fastener or other type of releasable fastener.

The ankle foot orthotic 54 includes a second strap 70 that has a primary end 72, a secondary end 74 and a primary surface 76 extending therebetween, and the second strap 70 is elongated between the primary end 72 and the secondary end 74. The primary end 72 is coupled to an inside surface 78 of the foot portion 20 of the boot 12 at a point that is located on the same side of the boot 12 with respect to the first strap 56. Additionally, the second strap 70 is centrally positioned between the leg portion 22 of the boot 12 and the toe 34 of the foot portion 20 of the boot 12. In this way the second strap 70 can extend over the 79 instep of the user's foot 14 when the user wears the boot 12.

The ankle foot orthotic 54 includes a primary mating member 80 that is coupled to the primary surface 76 of the second strap 70. The primary mating member 80 is positioned adjacent to the secondary end 74 of the second strap 70. The ankle foot orthotic 54 includes a secondary mating member 82 that is coupled to the inside surface 64 of the foot portion 20 of the boot 12 at a point that is located adjacent to the first edge 44 of the cut 38, The secondary mating member 82 is centrally positioned between the leg portion 22 of the boot 12 and the toe 34 of the foot portion 20 of the boot 12. Additionally, the primary mating member 80 is releasably mateable to the secondary mating member 82. Each of the primary mating member 80 and the secondary mating member 82 may comprise a hook and loop fastener or other type of releasable fastener.

An instep pad 84 that is positionable beneath the second strap 70 when the ankle foot orthotic 54 is worn to enhance comfort for the user's foot 14. The instep pad 84 has a first surface 86 and a perimeter edge 88, and the first surface 86 of the instep pad 84 is concavely arcuate with respect to the perimeter edge 88. In this way the first surface 86 can conform to curvature of the instep 79 of the user's foot 14. The perimeter edge 88 has a front side 90 and a back side 92, the back side 92 extends along a straight line and the front side 92 is rounded. Additionally, the instep pad 84 is comprised of a resiliently compressible material.

In use, the flap 18 is positioned in the open position to facilitate the user to wear the boot 12. The first strap 56 is extended across the user's lower leg 16 to facilitate the first mating member 66 to be mated to the second mating member 68. The second strap 70 is extended over the user's foot 14 to facilitate the primary mating member 80 to be mated to the secondary mating member 82. The flap 18 is positioned in the closed position and the first fastener 48 and second fastener 50 are mated to close the flap 18. In this way the boot 12 facilitates the ankle foot orthotic 54 to be employed by the user in a stylish manner that is visually appealing and that additionally conceals the ankle foot orthotic 54 from observers.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. An ankle foot orthotic assembly including an ankle foot orthotic being integrated into a boot thereby concealing the ankle foot orthotic on a user when said boot is worn, said assembly comprising:

a boot being configured to be worn on a user's foot having said boot configured to be extending upwardly on the user's lower leg, said boot having a flap being integrated therein, said flap being positionable in an open position thereby exposing an interior of said boot wherein said flap is configured to enhance the user's ability to position their foot and lower leg into said boot, said flap being positionable in a closed position wherein said boot is configured to be retained on the user's foot and lower leg, said boot having a foot portion being configured to surround the user's foot, said boot having a leg portion extending upwardly from said foot portion wherein said leg portion is configured to surround the user's lower leg;

a first fastener being coupled to said boot;

a second fastener being coupled to said flap, said second fastener being mateable to said first fastener for retaining said flap in said closed position, said second fastener being un-mateable from said first fastener to facilitate said flap to be positioned in said open position;

a cover being coupled to said boot, said cover covering said first fastener and said second fastener when said flap is in said closed position wherein said cover is configured to inhibit an observer from seeing said first fastener and said second fastener;

an ankle foot orthotic being integrated into said boot wherein said ankle foot orthotic is configured to engage the user's lower leg and the user's foot thereby facilitating said ankle foot orthotic to aid with foot drop syndrome in the user, said ankle foot orthotic being positioned inside said boot wherein said ankle foot orthotic is configured to be concealed from observers thereby enhancing the user's self-confidence;

wherein said leg portion has a top end being open to define an opening into said leg portion wherein said top end is configured to facilitate the user's lower leg to extend therethrough, said leg portion having an outward side being configured to be positioned on a lateral aspect of the user's lower leg when said boot is worn;

wherein said foot portion has a sole and a toe, said foot portion having an inward side being configured to be positioned on a medial side of the user's foot when said boot is worn;

wherein said boot has a cut extending therethrough, said cut having a first portion extending downwardly from said top end of said leg portion along said outward side of said leg portion, said cut having a second portion extending along said foot portion of said boot, said second portion being spaced from said sole, said second portion being oriented to extend along a line being oriented perpendicular to said first portion, said second portion extending around said toe to terminate on said inward side of said foot portion such that said first portion and said second portion of said cut defines said flap, said cut having a first edge and a second edge; and wherein said ankle foot orthotic comprises a first strap having a first end, a second end and a first surface extending therebetween, said first strap being elongated between said first end and said second end, said first end being coupled to an inside surface of a back quarter of said leg portion of said boot at a point being located on an opposite side of said leg portion with respect to said cut, said first strap being oriented to extend along a horizontal axis wherein said first strap is configured to be wrapped around a front portion of the user's lower leg when the user wears said boot, said first strap being spaced from said top end of said leg portion;

wherein the first fastener and the second fastener are a hook and loop fastener;

further comprising an instep pad detachable from the ankle foot orthotic assembly being positionable beneath said second strap when said ankle foot orthotic is worn wherein said instep pad is solely configured to conform to a portion of the curvature of an instep of the user's foot adjacent to said second strap;

wherein said ankle foot orthotic includes a first mating member being coupled to said first surface of said first strap, said first mating member being positioned adjacent to said second end of said first strap; and wherein said ankle foot orthotic includes a second mating member being coupled to said inside surface of said back quarter of said leg portion of said boot at a point being located adjacent to said first edge of said cut, said second mating member being positioned adjacent to said top end of said leg portion, said first mating member being releasably mateable to said second mating member.

2. The assembly according to claim 1, wherein said leg portion has a top end being open to define an opening into said leg portion wherein said top end is configured to facilitate the user's lower leg to extend therethrough, said leg portion having an outward side being configured to be positioned on a lateral aspect of the user's lower leg when said boot is worn, said leg portion having a back quarter, said back quarter being comprised of a rigid material wherein said back quarter is configured to assist with supporting the user's lower leg and the user's foot when said boot is worn.

3. The assembly according to claim 1, wherein said foot portion has a sole and a toe, said foot portion having an inward side being configured to be positioned on a medial side of the user's foot.

4. The assembly according to claim 1, wherein said first fastener is coextensive with said first edge of said cut.

5. The assembly according to claim 1, wherein said second fastener is coextensive with said second edge of said cut.

6. The assembly according to claim 1, wherein said cover is positioned on said foot portion of said boot, said cover being coextensive with said second portion of said cut, said cover extending downwardly over said second portion of said cut when said flap is in said closed position for concealing said first fastener and said second fastener along said foot portion of said boot.

7. The assembly according to claim 1, wherein said instep pad has a first surface and a perimeter edge, said first surface of said instep pad being concavely arcuate with respect to said perimeter edge wherein said first surface is configured to conform to curvature of the instep of the user's foot, said perimeter edge having a front side and a back side, said back side extending along a line, said front side being rounded.

8. An ankle foot orthotic assembly including an ankle foot orthotic being integrated into a boot thereby concealing the ankle foot orthotic on a user when said boot is worn, said assembly comprising: a boot being configured to be worn on a user's foot having said boot configured to be extending upwardly on the user's lower leg, said boot having a flap being integrated therein, said flap being positionable in an open position thereby exposing an interior of said boot wherein said flap is configured to enhance the user's ability to position their foot and lower leg into said boot, said flap being positionable in a closed position wherein said boot is configured to be retained on the user's foot and lower leg, said boot having a foot portion being configured to surround the user's foot, said boot having a leg portion extending upwardly from said foot portion wherein said leg portion is configured to surround the user's lower leg; a first fastener being coupled to said boot; a second fastener being coupled to said flap, said second fastener being mateable to said first fastener for retaining said flap in said closed position, said second fastener being un-mateable from said first fastener to facilitate said flap to be positioned in said open position; a cover being coupled to said boot, said cover covering said first fastener and said second fastener when said flap is in said closed position wherein said cover is configured to inhibit an observer from seeing said first fastener and said second fastener; an ankle foot orthotic being integrated into said boot wherein said ankle foot orthotic is configured to engage the user's lower leg and the user's foot thereby facilitating said ankle foot orthotic to aid with foot drop syndrome in the user, said ankle foot orthotic being positioned inside said boot wherein said ankle foot orthotic is configured to be concealed from observers thereby enhancing the user's self-confidence; wherein said leg portion has a top end being open to define an opening into said leg portion wherein said top end is configured to facilitate the user's lower leg to extend therethrough, said leg portion having an outward side being configured to be positioned on a lateral aspect of the user's lower leg when said boot is worn; wherein said foot portion has a sole and a toe, said foot portion having an inward side being configured to be positioned on a medial side of the user's foot when said boot is worn; wherein said boot has a cut extending therethrough, said cut having a first portion extending downwardly from said top end of said leg portion along said outward side of said leg portion, said cut having a second portion extending along said foot portion of said boot, said second portion being spaced from said sole, said second portion being oriented to extend along a line being oriented perpendicular to said first portion, said second portion extending around said toe to terminate on said inward side of said foot portion such that said first portion and said second portion of said cut defines said flap, said cut having a first edge and a second edge; and wherein said ankle foot orthotic comprises a first strap having a first end, a second end and a first surface extending therebetween, said first strap being elongated between said first end and said second end, said first end being coupled to an inside surface of a back quarter of said leg portion of said boot at a point being located on an opposite side of said leg portion with respect to said cut, said first strap being oriented to extend along a horizontal axis wherein said first strap is configured to be wrapped around a front portion of the user's lower leg when the user wears said boot, said first strap being spaced from said top end of said leg portion; wherein the first fastener and the second fastener are a hook and loop fastener; further comprising an instep pad detachable from the ankle foot orthotic assembly being positionable beneath said second strap when said ankle foot orthotic is worn wherein said instep pad is solely configured to conform to a portion of the curvature of an instep of the user's foot adjacent to said second strap; wherein said ankle foot orthotic includes: a second strap having a primary end, a secondary end and a primary surface extending therebetween, said second strap being elongated between said primary end and said secondary end, said primary end being coupled to an inside surface of said foot portion of said boot at a point being located on the same side of said boot with respect to said first strap, said second strap being centrally positioned between said leg portion of said boot and said toe of said foot portion of said boot wherein said second strap is configured to extend over the user's foot when the user wears said boot, wherein said ankle foot orthotic includes a primary mating member being coupled to said primary surface of said second strap, said primary mating member being positioned adjacent to said secondary end of said second strap, and, wherein said ankle foot orthotic includes a secondary mating member being coupled to said inside surface of said foot portion of said boot at a point being located adjacent to said first edge of said cut, said secondary mating member being centrally positioned between said leg portion of said boot and said toe of said foot portion of said boot, said primary mating member being releasably mateable to said secondary mating member.

\* \* \* \* \*